(12) United States Patent
Skarping et al.

(10) Patent No.: US 10,222,359 B2
(45) Date of Patent: Mar. 5, 2019

(54) METHOD FOR VERIFYING CORRECT FUNCTION OF SAMPLING EQUIPMENT

(71) Applicant: PROVTAGAREN AB, Hässleholm (SE)

(72) Inventors: Gunnar Skarping, Hässleholm (SE); Marianne Dalene, Hässleholm (SE)

(73) Assignee: PROVTAGAREN AB, Hassleholm (SE)

( * ) Notice: Subject to any disclaimer, the term of this patent is extended or adjusted under 35 U.S.C. 154(b) by 0 days.

(21) Appl. No.: 14/901,176

(22) PCT Filed: Jun. 30, 2014

(86) PCT No.: PCT/SE2014/050821
§ 371 (c)(1),
(2) Date: Dec. 28, 2015

(87) PCT Pub. No.: WO2014/209219
PCT Pub. Date: Dec. 31, 2014

(65) Prior Publication Data
US 2016/0139097 A1    May 19, 2016

(30) Foreign Application Priority Data

Jun. 28, 2013    (SE) ........................... 1350801

(51) Int. Cl.
*G01N 33/00*    (2006.01)
*G01N 1/24*    (2006.01)
(Continued)

(52) U.S. Cl.
CPC ............ *G01N 33/007* (2013.01); *G01F 1/88* (2013.01); *G01N 1/2247* (2013.01); *G01N 1/24* (2013.01);
(Continued)

(58) Field of Classification Search
CPC .................................................. G01N 33/0006
(Continued)

(56) References Cited

U.S. PATENT DOCUMENTS

| | | | |
|---|---|---|---|
| 4,246,788 A | 1/1981 | Olin et al. | |
| 4,268,224 A * | 5/1981 | Breuer | F04B 49/06 318/471 |

(Continued)

FOREIGN PATENT DOCUMENTS

| | | |
|---|---|---|
| EP | 1 441 272 | 7/2004 |
| JP | H02-093392 | 4/1990 |

(Continued)

OTHER PUBLICATIONS

International Search Report PCT/SE2014/050821, dated Oct. 28, 2014, 9 pages.*

(Continued)

*Primary Examiner* — Clayton E Laballe
*Assistant Examiner* — Kevin Butler
(74) *Attorney, Agent, or Firm* — Preti, Flaherty, Beliveau & Pachios LLP

(57) ABSTRACT

The invention relates to methods for verification of correct function of sampling equipment is disclosed, wherein said method comprises the steps of: a) providing a pump assembly (1) comprising an inlet (2) and an outlet (3), a flow channel (4) extending between said inlet (2) and outlet (3), a pump located along said flow channel (4) adapted to force an gas flow through said flow channel (4), a first mass flow sensor (6) located inside said flow channel (4), a first pressure sensor (7) located near said first mass flow sensor (6) adapted to measure a first pressure inside said flow channel (4), and a second pressure sensor (8) located outside said flow channel (4), said second pressure sensor (8) being adapted to measure a second pressure being the ambient (Continued)

atmospheric pressure, b) calculating the pressure difference between said first pressure and said second pressure c) calculating any error in an output signal from the mass flow meter by comparing said pressure difference with a value in a pre-calibrated table of mass flow output signal values as a function of said pressure difference, d) providing an error signal comprising a value of said calculated error if said value of said calculated error is above a predetermined threshold. The invention further relates to alternatives to said method.

17 Claims, 8 Drawing Sheets

(51) Int. Cl.
*G01F 1/88* (2006.01)
*G01N 1/22* (2006.01)
*G01N 1/40* (2006.01)
G01N 21/3504 (2014.01)
G01N 27/417 (2006.01)
G01F 15/02 (2006.01)
G01F 15/04 (2006.01)
G01F 1/74 (2006.01)

(52) U.S. Cl.
CPC ......... *G01N 1/405* (2013.01); *G01N 33/0006* (2013.01); *G01F 1/74* (2013.01); *G01F 15/02* (2013.01); *G01F 15/04* (2013.01); *G01F 15/046* (2013.01); *G01N 21/3504* (2013.01); *G01N 27/4175* (2013.01)

(58) Field of Classification Search
USPC .......................................................... 73/1.06
See application file for complete search history.

(56) References Cited

U.S. PATENT DOCUMENTS

| 4,549,566 | A | * | 10/1985 | Fujiwara | ................ | F04C 14/26 |
| | | | | | | 137/115.09 |
| 5,269,659 | A | * | 12/1993 | Hampton | ................ | F04B 49/06 |
| | | | | | | 417/12 |
| 5,542,284 | A | * | 8/1996 | Layzell | .............. | G01N 33/0006 |
| | | | | | | 73/23.2 |
| 5,996,422 | A | | 12/1999 | Buck et al. | | |
| 5,996,442 | A | | 12/1999 | Buck et al. | | |
| 6,155,790 | A | * | 12/2000 | Pyotsia | ................... | F04B 49/20 |
| | | | | | | 417/28 |
| 6,167,107 | A | | 12/2000 | Bates | | |
| 6,352,001 | B1 | * | 3/2002 | Wickert | ................... | G01F 1/44 |
| | | | | | | 73/861.52 |
| 7,700,045 | B2 | | 4/2010 | Skarping et al. | | |
| 8,034,624 | B2 | | 10/2011 | Skarping et al. | | |
| 2003/0031572 | A1 | * | 2/2003 | Tearle | ................ | F04B 43/0054 |
| | | | | | | 417/534 |
| 2004/0195038 | A1 | * | 10/2004 | Ikeda | ..................... | B62D 5/062 |
| | | | | | | 180/421 |
| 2006/0005607 | A1 | | 1/2006 | Blumke et al. | | |
| 2006/0239857 | A1 | | 10/2006 | Skarping et al. | | |
| 2010/0101302 | A1 | | 4/2010 | Graze, Jr. et al. | | |
| 2012/0052590 | A1 | | 3/2012 | Von Blumenthal | | |
| 2012/0222495 | A1 | | 9/2012 | Bates | | |
| 2012/0329166 | A1 | * | 12/2012 | Skarping | ................... | G01F 1/68 |
| | | | | | | 436/106 |
| 2016/0139097 | A1 | * | 5/2016 | Skarping | ................... | G01N 1/24 |
| | | | | | | 73/1.06 |

FOREIGN PATENT DOCUMENTS

| JP | H07-072050 | | 3/1995 | | |
| JP | H09-061434 | | 3/1997 | | |
| JP | 2003-155920 | A | 5/2003 | | |
| JP | 2006-046955 | A | 2/2006 | | |
| JP | 2006-300814 | A | 11/2006 | | |
| JP | 2013-073414 | A | 4/2013 | | |
| KR | 100872151 | | 12/2008 | | |
| WO | WO 00/75622 | A1 | 12/2000 | | |
| WO | WO 2007/129965 | A1 | 11/2007 | | |
| WO | WO 2011/108981 | | 9/2011 | | |
| WO | WO2011108981 | * | 10/2011 | ............... | G01N 1/22 |

OTHER PUBLICATIONS

Written Opinion International Search Agency PCT/SE2014/050821, dated Oct. 28, 2014, 10 pages.*
Flow Regulating System and Monitoring Device Comprising said Flow Reulating System for the Detection of Air Borne Analytes, WO2011108981 A1 Provtagaren AB et al., Sep. 9, 2011.*

* cited by examiner

METHOD FOR VERIFYING CORRECT FUNCTION OF SAMPLING EQUIPMENT

TECHNICAL FIELD

The present invention relates generally to a method for verifying correct function of sampling equipment. More particularly, the present invention relates to a method for verifying correct function of sampling equipment as defined in claims 1, 4 and 5.

BACKGROUND ART

There is a clear demand for the monitoring of air-borne compounds that can have health effects on exposed individuals. A great interest exists for compounds that have occupational exposure limit values, set by governmental bodies, to ensure that the levels of such compounds are satisfactory low. In many cases, it is not known what the air contaminants consist of and for this reason, it is of interest to learn more details about the nature of these "unknown" compounds and to reveal the identity of the most predominate ones. Another field of interest is to study and check the effect of measures with a view to reducing these levels in air, e.g. to check the "true" ventilation efficiency or other measures to control the air levels. Devices for this purpose can also be used for the monitoring of the quality of compressed air and air in respiratory protective devices. Other fields of application for such devices are e.g. the control of different volatile compounds present in food. Such compounds can be used as markers for degradation of certain food components or to monitor raw materials to ensure a satisfactory quality. Such devices may also be used to ensure that other compounds have not contaminated to food. In hospitals, such devices can be used to check the air levels of e.g. narcosis gases and to ensure that the personnel, patients or others are not exposed to toxic levels. Chemical warfare agents are compounds that need to be checked for in order to reveal the presence thereof and to ensure that individuals are not exposed.

In environmental analysis there is a need to monitor the quality of air in cities, public places and in the nature. One purpose is to obtain background data for statistical studies and to check if the levels are below the levels set by national and international bodies. They can also be used to check if the emission of industrial pollutants results in exposure in the nature or in populated areas. The achieved data can have an impact on decisions and interpretation of a certain situation. There is therefore a demand of a satisfactory high quality of the data.

There are many examples of air pollutants that occur in both gas and particle phase. Of special interest are the size fractions that have the ability to reach the lower respiratory tract. There are reasons to believe that the toxicology is different depending on not only the chemistry as such but also on the distribution on different target organs in the body of humans. There is a need to know more about the exposure to the respirable particle fraction present in air.

Numerous devices exist for the monitoring of air-borne compounds and there is a great variety of technology used. In principle, the devices can be grouped in selective and non-selective devices. Non-selective devices give a response for several compounds and do not differentiate between two or several compounds and may also result in false positive results. Such devices are today still used, possibly due to the low cost. In many applications, false positive results can give rise to a high cost for the user, if costly measures are performed from invalid data.

Selective devices give a certain response for a selected compound or a group of compounds. Other present compounds do not interfere with the result. The frequency of false positive results will be much less as compared to non-selective monitoring. The quality of the data obtained is essential. Typical factors that describe the quality of the data are: repeatability, reproducibility, linearity (calibration graph characteristics with intercept and background), detection limit and quantification limit. In addition, knowledge regarding the interference from other compounds is necessary. It needs to be mentioned that a certain compound can influence the result even if the compound does not itself give rise to a response.

There are several drawbacks with the present types of instruments. For Photo Ionization Detector (PID) and Flame Ionization Detector (FID), identification of the individual chemicals is not possible. PID and FID detectors measure the sum of VOC (Volatile Organic Compounds). Infrared detectors suffer from problems with inferences. IR detectors are not possible to use when monitoring VOCs at low concentration when other interfering compounds are present.

For direct monitoring using GC-PID (e.g. VOC71M from Environment s.a.; www.environnementsa.com) and the GC-DMS instrument (e.g. Sionex Inc., Bedford, Mass., USA) there are limitations leading to inaccurate identification and quantification of analytes, and external complementary pre or post-calibration have to be made. For the existing products it is not possible to perform calibration automatically in the field. Further, there are problems with the occurrence of a non-linear relation between the sampling time and determined concentrations, which thereby disables long time sampling if the amount exceeds the calibration range. Further, when a volume is collected it needs to be calibrated to a volumetric volume and possibly corrected for the ambient temperature and air pressure. The sampling of a volume in a certain sampling volume container or on a sorbent followed by thermal desorption (in the case of a sorbent) and thereafter injecting the collected compounds on the GC the chromatographic peaks will be broadened in a way that the resolution of the chromatography will be affected.

A sampling device for analysis of air pollutants, more precisely polyurethane products, is disclosed in WO 00/75622, and further developments thereof are disclosed in WO 2011/108981 and in WO 2007/129965. The sampling devices, also called samplers, disclosed in these publications collect the probed chemical in a two-step process. A fluid in which the amount of a chemical is to be measured is pumped through the sampling device using a controlled flow. The chemical substance of interest present in the gas phase of the fluid is collected in an adsorption tube using a regent coated on the surfaces present inside the tube. The flow of fluid is further pumped from the adsorption tube to and through a filter impregnated with the same reagent. The chemical substance in solid form or adhered to particles in the fluid is collected in the filter.

An important parameter in this area is the gas flow containing the compound to detect, i.e. the analyte, in the apparatus used for the detection. During the sampling of compounds in air it is of importance to be able to control and log the flow and volume of the acquired amount of air through the sampling device as there is a direct correlation between the contents in a sample and the air volume collected. Taking several samples simultaneously is also of importance for three reasons, more precisely for increasing the accuracy of a certain sample, for detecting erroneous samples, and for acquiring different compounds simultaneously. When handling sampling results, it is also important to be able to track how the sample was collected, the time, the flow, the temperature, the pressure, and the humidity.

Existing solutions to maintain a stable flow during sampling do not prove to maintain a stable flow over time and require field calibration. The flow speed needs to be calibrated before and after sampling to ensure that the sampling speed is correct and have not changed over time. A logging functionality is also often missing.

Some existing solutions where a differential pressure sensor indicates if a change in the flow system back pressure has occurred, adjusts the pump control signal to compensate for this. However, this solution has proven to give drift errors over time, and a calibration with an external flow meter is required in order to set a certain flow rate of its pump.

Another existing solution has a logging function, an ability to transfer logged data to a PC, and an ability to control the flow via a display and buttons. Tests on such pumps did not concur with its specifications, as the pumps did not manage to keep a stable flow due to the fact that a sampler inducing a certain backpressure was attached to it.

A problem with existing pump systems is that the flow sensors incorporated in them may fluctuate with the temperature of the flow sensor electronics. Most flow sensors, using different techniques for the actual measurement of gas flow, have an output voltage signal corresponding to the measured flow. The output signal is however easily affected by the temperature of the electronic components in the flow sensor.

A further problem with the pumps for sampling purposes of the prior art is that the calibration of the pump mass flow sensor and thereby its measurement results is/are degraded relatively fast due to wear and damages to the sensors of the pump and to the pump engine. The pumps are often used in rough conditions at industrial work places and often outdoors.

In view of this, there is a great demand for an improved pump assembly for monitoring devices for the above mentioned detection of air-borne compounds, and for a pump that has the ability to deliver adequate pumping performance required for accurate measurements.

In that context there is further a demand for automatically detection of defects in sampling equipment e.g. in a pump assembly and a sampling device, or other devices used in sampling.

SUMMARY OF THE INVENTION

It is an object of the present invention to improve the current state of the art, to solve the above problems, and to provide an improved method for the detection of defects in sampling equipment. These and other objects are achieved by a method for verification of correct function of sampling equipment, wherein said method comprises the steps of a) providing a pump assembly comprising an inlet and an outlet, a flow channel extending between said inlet and outlet, a pump located along said flow channel adapted to force a gas flow through said flow channel, a first mass flow sensor located inside said flow channel, a first pressure sensor located near said mass flow sensor adapted to measure a first pressure inside said flow channel, a second pressure sensor located outside said flow channel, said second pressure sensor being adapted to measure a second pressure being the ambient atmospheric pressure, b) calculating the pressure difference between said first pressure and said second pressure, c) calculating any error in an output signal from the mass flow meter by comparing said pressure difference with a value in a pre-calibrated table of mass flow output signal values as a function of said pressure difference, and d) providing an error signal comprising a value of said calculated error if said value of said calculated error is above a predetermined threshold.

By measuring the difference between the pressure in the flow channel and the ambient pressure, the thereby induced error in a mass flow measurement is calculated. When no equipment is attached to the pump assembly, and the back pressure thus is known, the output signal from the first mass flow sensor (6) may be adjusted if the calculated error is below said predetermined threshold. The resulting mass flow signal will be a combination of the mass flow signal from the first mass flow sensor and the mass flow calculated as a function of said pressure difference, e.g. a weighted mean. The error occurs due to that the mass flow sensor in the pump assembly has been calibrated at a certain pressure. However, when the pump assembly is used with external equipment, a backpressure from connected equipment may cause the pressure inside the flow channel of the pump assembly to change. Using the inventive method, this error can be measured and the value thereof is provided via an error signal. The error signal with the value of the error may be used for adjusting the output signal from the mass flow sensor to compensate for the calculated error. In that way the pump assembly will measure the correct mass flow and be able to pump the correct volume flow through the equipment it is connected to, regardless of backpressure values affecting the mass flow meter. A correct flow measurement is especially important when the pump assembly is connected to a sampling device, through which the gas flow is drawn by use of the pump assembly.

The sampling device is used for sampling of analytes in the gas flow. An efficient and controlled sampling of both gas and particles in the gas flow is required, e.g. to control the concentration of hazardous compounds in gas at a work place or public area. The sampling device has the ability to differentiate between the analyte present in the gas phase and/or in the particle phase of the gas flow. Such a sampling device having this differentiating ability is disclosed in WO 00/75622 and in US-2006-0239857, which documents are hereby included by reference.

The gas that is to be measured and forced through the pump is e.g. breathing air, modified breathing air, helium, hydrogen, nitrogen, oxygen, argon, or mixtures thereof.

According to one aspect of the invention a method is provided for verification of correct function of sampling equipment, wherein said method comprises the steps of:

a) providing a pump assembly (1) comprising: an inlet (2) and an outlet (3), a flow channel (4) extending between said inlet (2) and outlet (3), a pump located along said flow channel (4) adapted to force a gas flow through said flow channel (4), a pump operational speed sensor (11), a first mass flow sensor (6) located inside said flow channel (4), a first pressure sensor (7) located near said first mass flow sensor (6) adapted to measure a first pressure inside said flow channel (4), and a second pressure sensor (8) located outside said flow channel (4), said second pressure sensor (8) being adapted to measure a second pressure being the ambient atmospheric pressure;

b) measuring a first property being any one of the three properties: a mass flow using the first mass flow sensor (7), a differential pressure using said first pressure sensor and said second pressure sensor, and a pump operational speed using said pump operational speed sensor (11);

c) measuring a second property of said three properties, the second property being different from the first property;

c) calculating an approximated value of the third property not measured in a) and b) from the properties measured in a) and b);

d) measuring the third property not measured in a) and b);

e) calculating a difference between the approximated value of the third property and the measured value of the third property;

f) providing an error signal indicating that said sampling equipment does not function correctly if said calculated difference exceeds a predetermined value. The error signal thus indicates that at least one of the sensors measuring the mass flow, differential pressure, or pump operational speed is malfunctioning, i.e. a relationship between Flow, differential Pressure, and pump operational Speed (called the FPS relationship). A sudden deviation of above about 5% from a previous measured value in a measurement session, e.g. measured one second to 10 minutes ago, indicates malfunction. If the error signal indicates an error of more than 10% deviation from values set at the factory calibration, but deviates less than 5% from recent measurements, the error is probably due to wear and tear of the pump assembly. Both of these error types are preferably displayed for the operator of the pump assembly. The ability to measure the flow using the pump operational speed creates the opportunity to check that the mass flow sensor measurement results are close to expected values. This check is preferably made when starting up the pump before the measurements so that a malfunctioning mass flow sensor is detected before measurements have been conducted. As pointed out above, e.g. a measurement using a sampling device for gas contamination measurements requires an accurate flow value through the sampler to be able to calculate a concentration of the contamination in the gas. A measurement taken made using a pump with a malfunctioning flow sensor is therefore useless. Thus, it is essential to detect such an error before sometimes time consuming measurements are conducted.

As the pump assembly via the pump operational speed sensor has the ability to measure the mass flow, in the ideal case producing the same value as the first mass flow sensor does, if compensated by the measured pressure deviation in the flow channel compared to the ambient pressure. If the first mass flow sensor is not corrected, any deviations between flow measurements will be due to a pressure difference between the flow channel and the ambient atmosphere. A value of the pressure difference can thus be calculated by a difference between the flow estimated by the pump operational speed sensor and the flow measured with the first mass flow sensor. If the measured pressure, as measured with the ambient pressure sensor and the first pressure sensor inside the flow channel, differs from the calculated pressure difference, one of the pressure sensors is likely damaged. A warning can then be provided to an operator of the pump assembly. The operational speed may be the rotational speed of the pump engine. In case of a rotary pump, the rotational speed may be the rotation speed of the pump rotor.

According to a further aspect of the invention a method is provided for verification of correct function of sampling equipment, wherein said method comprises the steps of:

a) providing a pump assembly (1) comprising an inlet (2) and an outlet (3), a flow channel (4) extending between said inlet (2) and outlet (3), a pump located along said flow channel (4) adapted to force a gas flow through said flow channel (4), a pump operational speed sensor (11), a pump current consumption sensor (16) measuring a power consumption of said pump, a first mass flow sensor (6) located inside said flow channel (4), a first pressure sensor (7) located near said first mass flow sensor (6) adapted to measure a first pressure inside said flow channel (4), and a second pressure sensor (8) located outside said flow channel (4), said second pressure sensor (8) being adapted to measure a second pressure being the ambient atmospheric pressure;

b) measuring a first property being any one of the three properties: a pump current consumption sing said pump current consumption sensor (16), a differential pressure using said first pressure sensor and said second pressure sensor, and a pump operational speed using said pump operational speed sensor (11);

c) measuring a second property of said three properties, the second property being different from the first property;

d) calculating an approximated value of the third property not measured in a) and b) from the properties measured in a) and b);

e) measuring the third property not measured in a) and b);

f) calculating a difference between the approximated value of the third property and the measured value of the third property;

g) providing an error signal indicating that said sampling equipment does not function correctly if said calculated difference exceeds a predetermined value.

The error signal thus indicates that at least one of the sensors measuring the differential pressure, pump current consumption or pump operational speed is malfunctioning, i.e. a relationship between pump Current consumption, differential Pressure, and pump operational Speed (named the CPS relationship). A sudden deviation of above about 5% from a previous measured value in a measurement session, e.g. measured one second to 10 minutes ago, indicates malfunction. If the error signal indicates an error of more than 10% deviation from values set at factory calibration, but deviates less than 5% from recent measurements, the error is probably due to wear and tear of the pump assembly. Both of these error types are preferably displayed for the operator of the pump assembly.

According to a further aspect of the invention the above-mentioned methods (the methods relating to the FPS and CPS relationships) further comprises the steps of:

a) if the method relating to the FPS relationship provides an error signal and also the method relating to the CPS relationship provides an error signal, providing a third error signal indicating that the pressure sensor or the pump is damaged;

b) if the method relating to the FPS relationship provides an error signal while the method relating to the CPS relationship does not provide an error signal, providing a fourth error signal indicating uncertain flow measurements; and c) if the method relating to the FPS relationship does not provide an error signal while the method relating to the CPS relationship provides an error signal, providing a fifth error signal indicating an error in the pump.

By measuring the mass flow using the mass flow sensor, estimating the flow by the pump operational speed, measuring said differential pressure and estimating the differential pressure using the pump current consumption it is possible to not only detect a measurement error, but also decide which sensor is malfunctioning. That is, by coupling the FPS relationship and the CPS relationship, the sensor being the source to the error can be determined and may be presented to a user or logged for later evaluation.

According to a further aspect of the invention the pump assembly further comprises an inlet filter, and an outlet filter, and the method further comprises the step of providing an error signal if the calculated pressure difference is below a pre-determined value, thereby indicating a broken inlet or outlet filter of the pump assembly. A sudden deviation of more than about 5% from a previous measured value in a measurement session, e.g. measured one second to 10 minutes ago, indicates malfunction. If the error signal indicates an error of more than 30% deviation from values set at the factory calibration, but deviates less than 5% from recent measurements, the error is probably due to wear and tear of the pump assembly. Both of these error types are preferably displayed for the operator of the pump assembly. By detecting broken filters before measurements are initiated, the pump assembly is saved from wear and extra service. Thereby costs can be saved.

Regarding the aspect of the invention where a sampling device is connected to the pump assembly, the invention comprises the further steps of providing an error signal if the calculated pressure difference exceeds a pre-determined value, thereby indicating a clogged or blocked sampling device, and providing an error signal if the calculated pressure difference is below a pre-determined value, thereby indicating a broken and/or leaking sampling device. If the pressure difference is more than 10% lower than expected, an indication is provided that the sampler is leaking. This feature makes it possible to detect broken sampling devices, which is an essential feature when measurements are taken at remote locations e.g. where it is expensive or even impossible to return and redo the failed measurement. The value of the calculated pressure difference may also be used to estimate which type of sampling device is connected since different types of sampling devices present different back pressure to the pump assembly. If the sampling device type is possible to determine, the pump assembly may use pre-set values for flow and measurement times specific to the type of sampling device that is used.

Regarding a further aspect of the invention where a sampling device is connected to the pump assembly, the method may further comprise the steps of measuring the backpressure induced by the sampling device, calculating its restriction and evaluating the condition of the sampling device, and logging said restriction and said evaluated condition to a memory for information and diagnostic purposes. The logged values may then be read at a later stage to provide further information regarding the measurement made using the sampling device.

According to a still further aspect of the invention the pump assembly comprises an ambient temperature sensor, wherein the method further comprises the step of measuring the ambient temperature with the ambient temperature sensor, measuring the temperature in the flow channel using a reference temperature measurement provided by the mass flow sensor, calculating the temperature difference between the measured ambient temperature and the measured reference temperature in the flow channel, and providing an error signal if the calculated temperature difference is above a predetermined threshold. The ambient temperature sensor may be used to increase the accuracy of the correction of the flow measurement value when e.g. converting the mass flow to a volume flow. The above method makes it possible to detect if either the ambient temperature sensor or the reference temperature sensor of the mass flow meter is broken. The method may further comprise the step of providing the option of manually setting the ambient temperature to a certain value. If the above method indicate that the ambient temperature sensor is broken, the temperature value to be used in calculations may be set manually by the operator of the pump assembly, e.g. by looking at a normal thermometer close by or checking the weather forecast.

According to a still further aspect of the invention the pump assembly further comprises an ambient temperature sensor, wherein the method further comprises the step of calculating the volumetric flow from the measured mass flow and the measured ambient temperature by use of the ideal gas law. This is an important step in the process of sampling of the gas contamination concentration, as it is impossible to calculate a concentration without a value of the measured volume (corresponding to the volume flow times the measurement time).

According to a still further aspect of the invention a second mass flow sensor is detachably connected to said outlet or inlet. This is followed by measuring a first mass flow with the first mass flow sensor and a second mass flow with the second mass flow sensor, calculating the difference between the values of said first and second mass flows, and providing an output signal representing said calculated difference. If such a reference measurement produces an error signal, the first mass flow meter of the pump assembly has to be re-calibrated. This can, however, be achieved automatically by adjusting the output signal of the first mass flow meter to compensate for said calculated difference. The external mass flow sensor may be connected via a USB port in the pump assembly and thereby be controlled by the CPU of the pump assembly. The external mass flow sensor may optionally also be built into the pump assembly, and only be used for occasionally checking the calibration of the first mass flow meter.

According to a still further aspect of the above-mentioned method at least one of the values of the ambient temperature, first mass flow, second mass flow, first pressure, second pressure, reference temperature and calculated errors is/are logged by writing the time and value to a memory comprised in said pump assembly. Logging of values relating to the pump operation makes it possible to look back if e.g. a sampling of air pollution produces an unreasonable result. The log files of the pump assembly may be checked for deviating values. If such a deviating value is found it may be possible to compensate for any error and still use the sampling without having to redo it.

According to a still further aspect of the above-mentioned method one or more pump assemblies are communicatively connected to a controlling device. The pump assemblies may also or alternatively be communicatively connected to each other. Measurement results may then be compared between different pump assemblies presenting further possibilities of detecting whether the pump assembly sensors functions correct or not. The communicatively connection may be achieved wireless over e.g. WLAN, Bluetooth or Zigbee, or wired over e.g. USB or Ethernet.

According to a further aspect of the invention said pump assembly further comprises a CPU (central processing unit), and a memory, wherein all method steps are instructions in a computer program stored on said memory, said computer program being executed by said CPU, and wherein all calculations steps are performed by use of said CPU.

Generally, all terms used in the claims are to be interpreted according to their ordinary meaning in the technical field, unless explicitly defined otherwise herein. All references to "a/an/the [element, device, component, means, step, etc.]" are to be interpreted openly as referring to at least one instance of said element, device, component, means, step, etc., unless explicitly stated otherwise. The steps of any method disclosed herein do not have to be performed in the exact order disclosed, unless explicitly stated.

As used herein, the term "comprising" and variations of that term are not intended to exclude other additives, components, integers or steps.

BRIEF DESCRIPTION OF THE DRAWINGS

The above objects, as well as additional objects, features and advantages of the present invention, will be more fully appreciated by reference to the following illustrative and non-limiting detailed description of preferred embodiments of the present invention, when taken in conjunction with the accompanying drawings, wherein.

DETAILED DESCRIPTION OF PREFERRED EMBODIMENTS OF THE INVENTION

Figure 1:
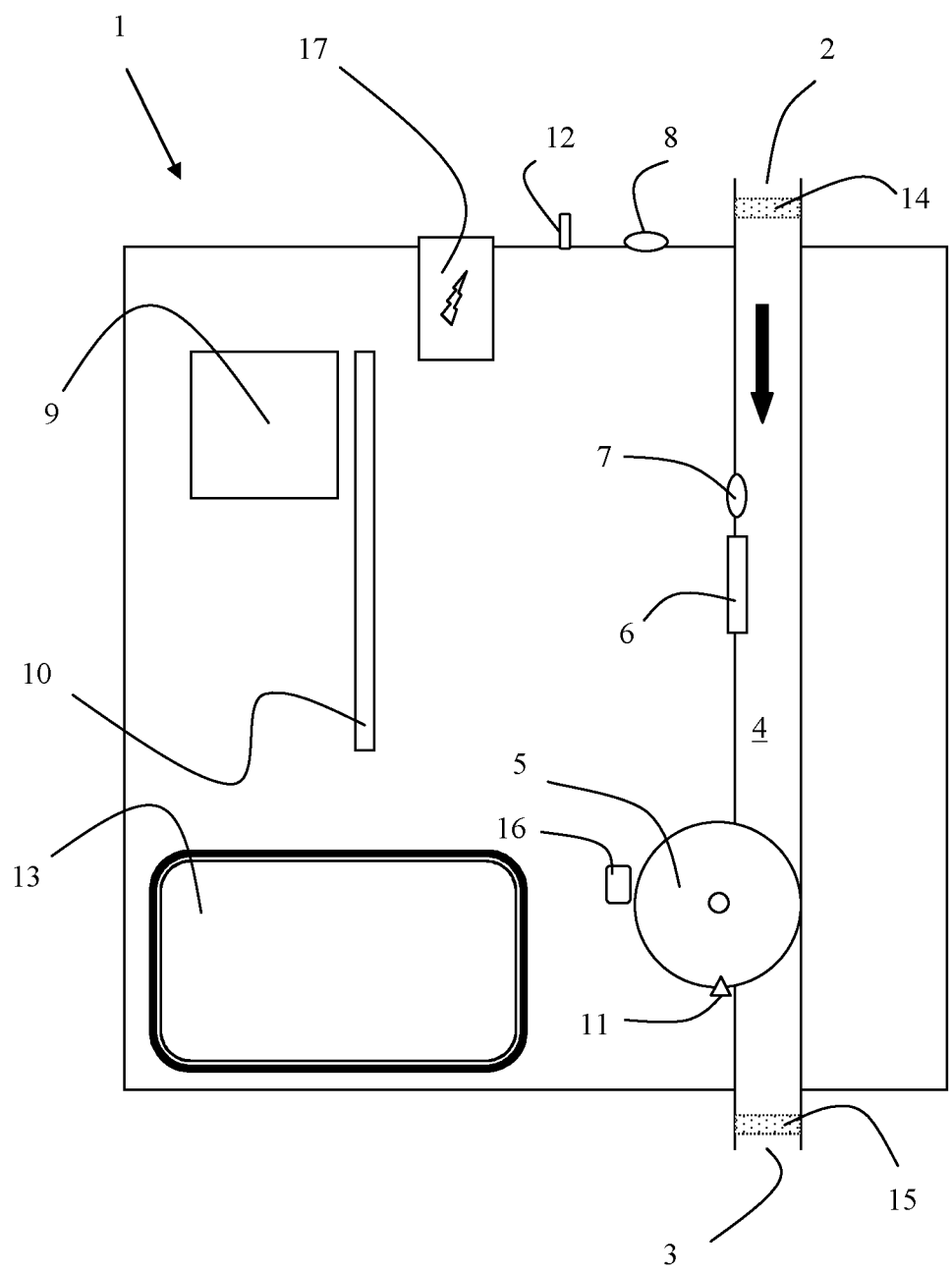
FIG. 1 is a schematic illustration of the pump assembly of the present invention.

The pump assembly 1 according to the present invention is defined as a pump 5, e.g. a rotational vane pump or a membrane pump, but any suitable pump is feasible, and equipment 4, 6, 7, 8, 9, 10, 11, 12, 13, 14, 15 for making the pump to produce an accurately determined flow, as required for a sampling measurement. FIG. 1 is a schematic illustration of the pump assembly 1 according to one embodiment of the present invention. The pump assembly 1 has a flow channel 4 having an inlet 2 and an outlet 3. Gas, e.g. in the form of breathing air or modified breathing air, is drawn through the flow channel 4 by a pump 5. The pump can be of any sort that is able to stand the back pressure of connected equipment, e.g. a rotary vane pump or a membrane pump. The mass flow of gas flowing through the flow channel 4 is measured by a mass flow sensor 6. Adjacent to the mass flow sensor 6 is a first pressure sensor 7, measuring the pressure in the flow channel 4. A second pressure sensor 8 is located on the outside of said flow channel 4 and said pump assembly 1. The second pressure sensor 8 thus measures the ambient pressure. The pump assembly is controlled by a CPU 9, wherein the CPU 9 uses a memory 10 to store control algorithms and data. The pump 5 has a operational speed sensor 11, measuring the motor speed of the pump. The pump assembly 1 is further equipped with an ambient temperature sensor 12, measuring the ambient temperature. The pump assembly further has a display 13 for presenting information and options to an operator of the pump assembly. The display is preferably a touch display to provide interaction with the pump assembly. In case of a non-touch display, buttons (not shown) are present near the display. The flow channel 4 of the pump assembly 1 further has an inlet filter 14 and an outlet filter 15.

The pump assembly in FIG. 1 further has a communication unit 16 providing means for communication with other units, as e.g. another pump assembly, a computer or any other equipment that could be useful to connect to the pump assembly. The communication may be via USB, wired network, or wireless network such as Bluetooth or WLAN.

Figure 2:
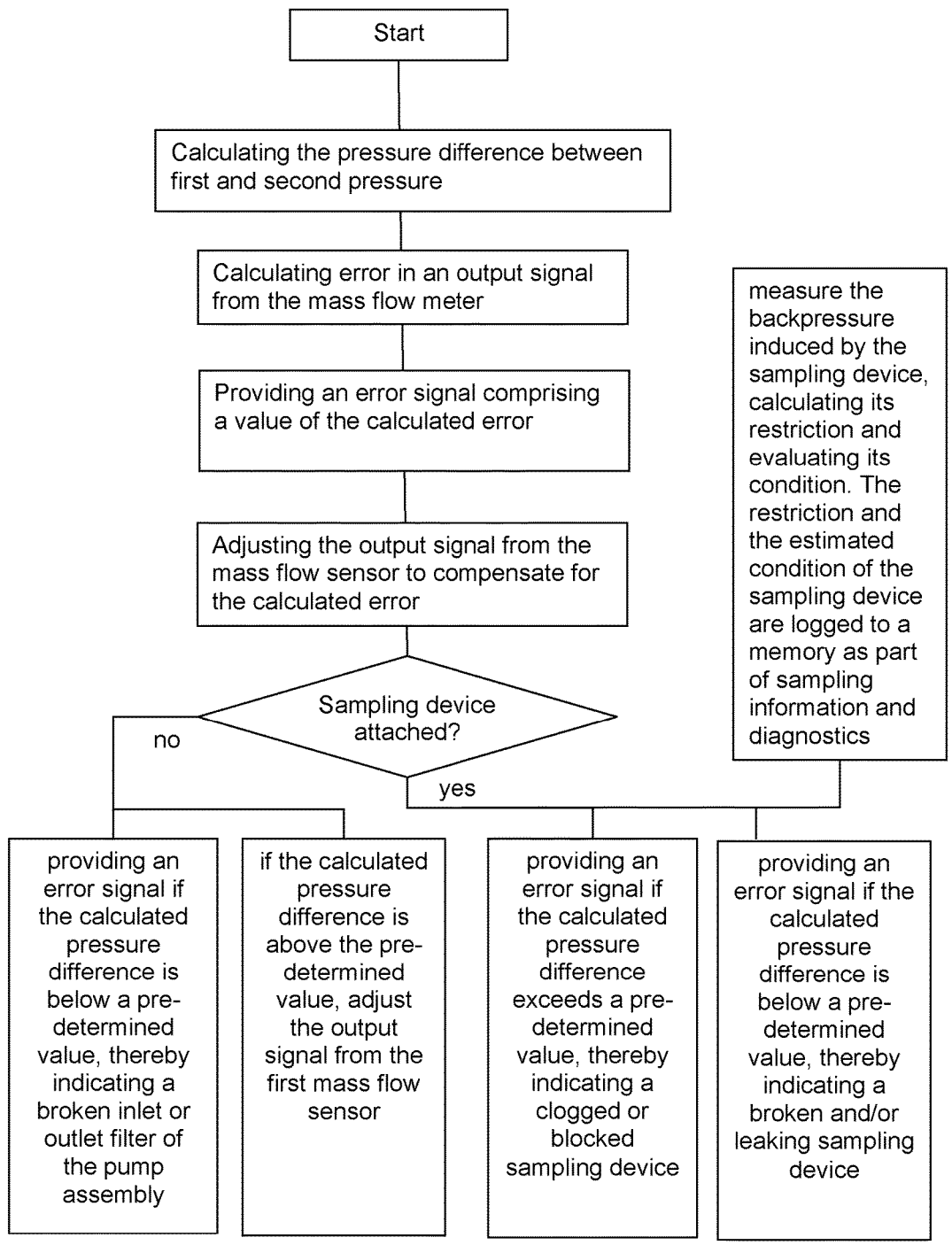
FIG. 2 is a flow chart showing how the mass flow sensor measurements may be corrected by knowing the pressure difference between the flow channel and the ambient atmosphere. The chart further shows how the method may be used for determining broken filters on the pump assembly, for detecting a clogged or broken sampling device, attached to the pump assembly, and for detecting leakage in the sampling device.

FIG. 2 is a flow chart showing how the mass flow sensor 6 measurements may be corrected by knowing the pressure difference between the flow channel 4 and the ambient atmosphere, leading to increased accuracy when measuring during e.g. a sampling of air. The chart further shows how the method may be used for determining broken filters 14, 15 on the pump assembly. When starting the pump assembly 1 and before attaching any equipment to the pump assembly 1, such as a sampling device (not shown), the operator is presented with the choice of checking if the inlet filter 14 or the outlet filter 15 is OK. This may e.g. be presented to the user at the startup of the pump assembly 1. The CPU 9 will start the pump and calculate the pressure difference between the two pressure sensors. If the pressure difference is less than expected, i.e. less than a predetermined threshold, the display will alert the operator of the pump assembly 1 that a possible filter damage has occurred.

The same principle can be used for detecting leakage in the sampling device. After attachment of a sampling device to the pump assembly, the operator may, via the display 13, be presented with the choice to test the sampling device for leakage, provided that the type of sampler used is known to the pump assembly. The pressure difference is measured and if it is lower than expected, i.e. lower than a predetermined threshold, the operator is warned that a leakage in the sampling device or its coupling to the pump assembly 1 is present. In the same way, if a sudden drop in back pressure occurs during sampling, the pump assembly will indicate for the operator that a leakage has occurred.

The same principle can in a similar way be used for detecting a clogged or broken sampling device after attachment of such a device to the pump assembly 1. After attachment of the sampler, the CPU 9 in the pump assembly 1 will constantly look for too high pressure differences. If an unexpected high pressure difference, or a back pressure, is detected, the operator is told, via the display 13, that a probable clogging of or other damage to the filter has occurred.

Measured backpressure induced by the sampler may also be used for calculating the restriction and evaluating the condition of the sampling device. The restriction and the estimated condition of the sampling device are logged to a memory as part of sampling information and diagnostics.

Figure 3:
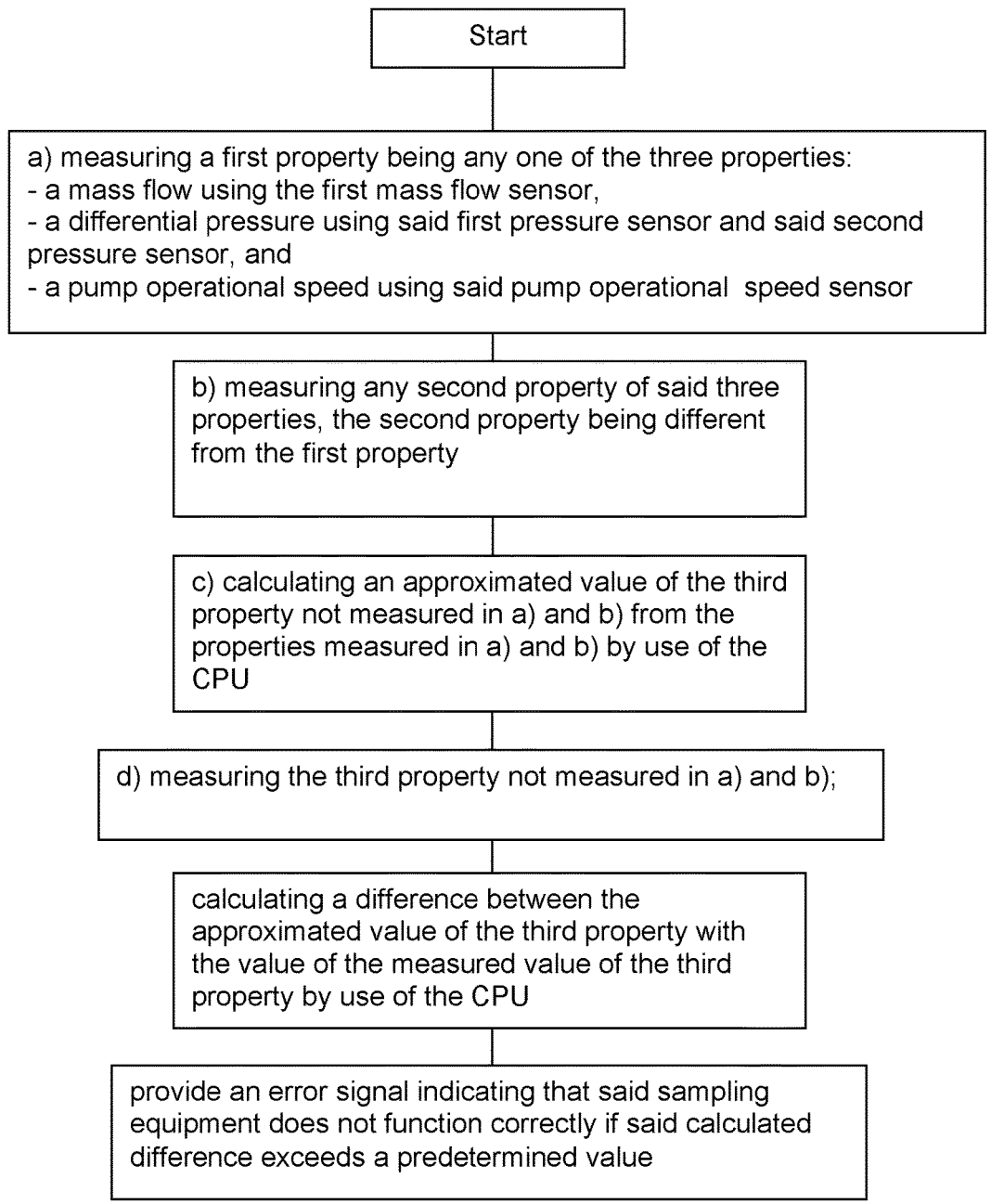
FIG. 3 is a flow chart showing how a relationship between the operational speed sensor of the pump, a measurement of the differential pressure between the first and second pressure sensors and the mass flow sensor can be used for detecting errors in the mass flow detector.

FIG. 3 is a flow chart showing how a operational speed sensor 11 of the pump 5 can be used together with the pressure sensors and the mass flow sensor of the pump assembly 1 for detecting errors in any one of these sensors. This can be done in three ways.

The CPU 9 uses the operational speed to calculate a flow and checks the measured temperature difference between the two pressure sensors 7, 8. The CPU 9 then knows the value to expect from the mass flow sensor 6 (the expected value is not corrected for the pressure difference). If the expected mass flow measured by the mass flow sensor 6 differs from the expected by more than a certain threshold, the operator will warned that at least one sensor is damaged and/or need recalibration, the error message being dependent on the magnitude of the detected error.

The CPU 9 uses the pump operational speed to calculate a flow. The flow should be equal to the measured mass flow as measured by the mass flow sensor 6, when corrected for the pressure difference. The difference between the calculated flow obtained from the operational speed sensor 11 and the mass flow measured by the mass flow sensor 6 can thus be used to check if the differential pressure measurement is reasonable. If the differential pressure deviate more than expected, i.e. more than a pre-determined threshold, the operator is provided with an error message indicating at least one damaged sensor.

The CPU 9 can calculate a corrected mass flow from the signal from the mass flow sensor 6 and the measurement of the pressure difference. That value should be equal to a calculated flow calculated using the operational speed sensor 11. If the latter differs more than a predetermined amount from the corrected mass flow sensor reading, an error signal that at least one sensor is damaged is presented to the operator.

Figure 4:
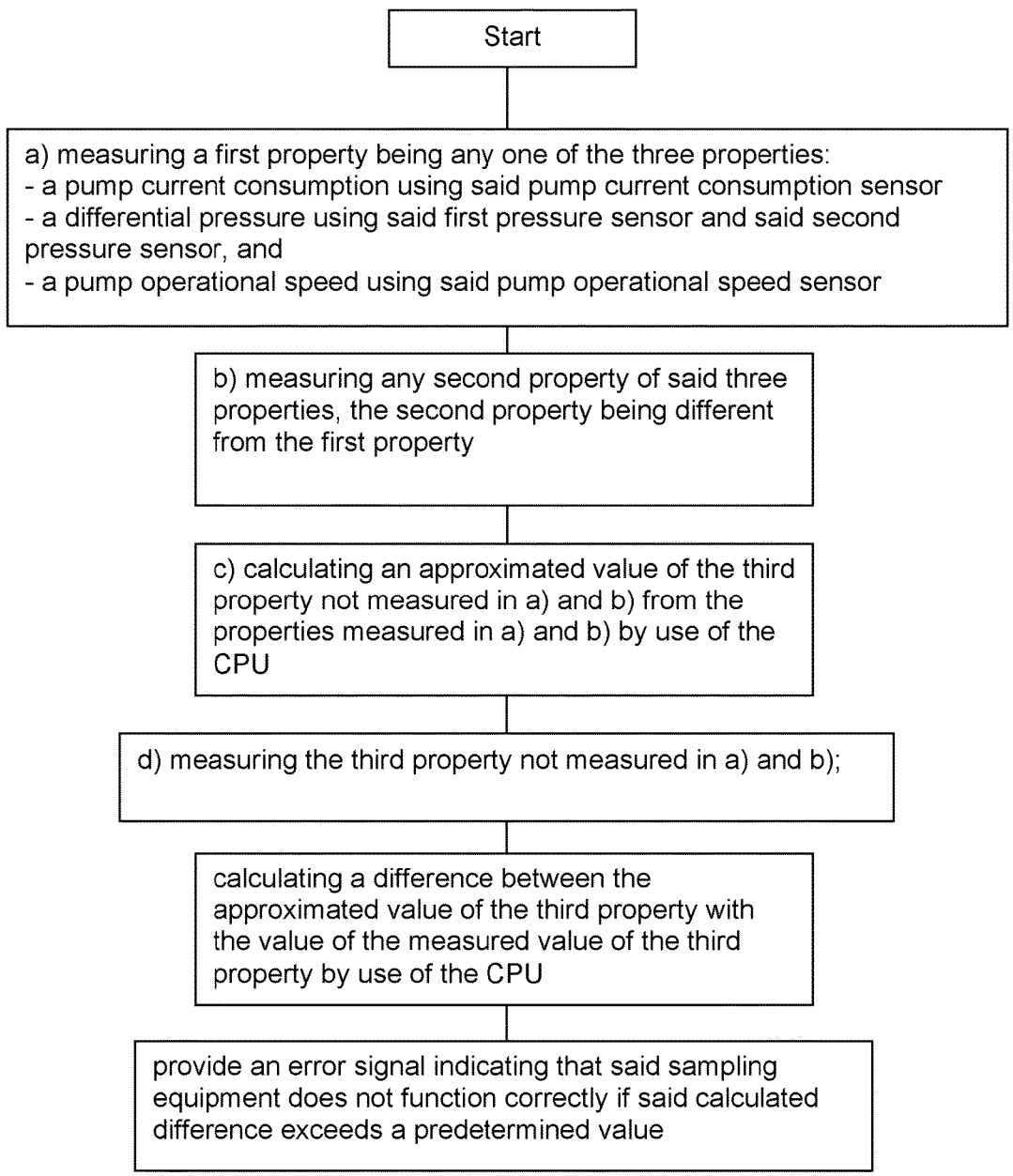
FIG. 4 is a flow chart showing how a relationship between the pump current consumption, a measurement of the differential pressure between the first and second pressure sensors and the operational speed sensor can be used for detecting errors in said measurements.

FIG. 4 is a flow chart showing how a relationship between the pump current consumption, a measurement of the differential pressure between the first and second pressure sensors and the operational speed sensor can be used for detecting errors in said measurements. In analogy with the described method of FIG. 3, a malfunctioning sensor can be detected by calculating the third property from measurements of the other two and compare the calculated property with a measurement using the sensor for that property. If the calculated value of the third property differs more than a predetermined value from the measured value for the third property, an indication that at least one of the sensors for the three properties is malfunctioning and need maintenance or recalibration.

Figure 5:
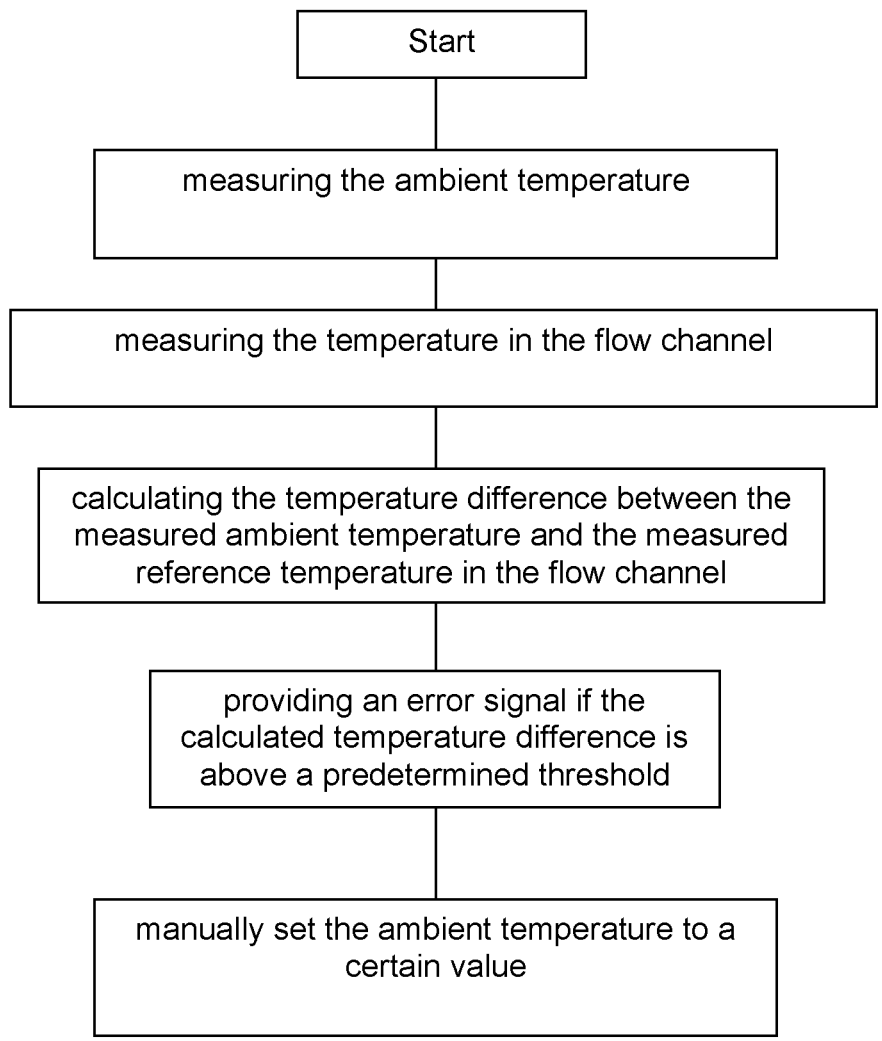
FIG. 5 is a flow chart showing how an ambient temperature sensor can be used together with the pressure sensors, and an internal temperature sensor located in the flow channel provided by the mass flow sensor of the pump assembly for detecting errors in temperature measurement.

FIG. 5 is a flow chart showing how an ambient temperature sensor 12 can be used together with the pressure sensors 7,8, and an internal temperature sensor located in the flow channel provided by the mass flow sensor 6 of the pump assembly 1 for detecting errors during a temperature measurement. If an error is detected it is displayed to the operator of the pump assembly 1.

Figure 6:
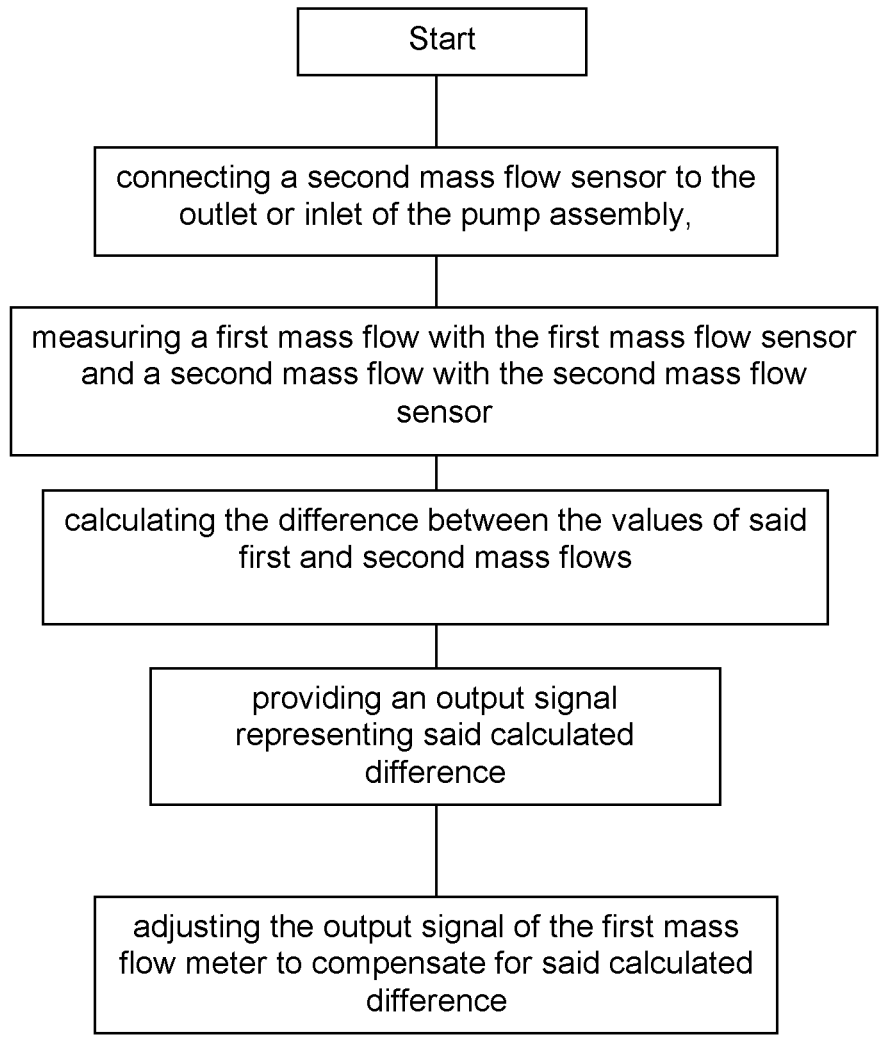
FIG. 6 is a flow chart showing how an additional external mass flow sensor can be used to detect calibration errors of the mass flow sensor in the pump assembly and how the calibration can be corrected if needed.

FIG. 6 is a flow chart showing how an additional external mass flow sensor (not shown) can be used to detect calibration errors of the mass flow sensor 6 in the pump assembly 1 and how the calibration can be corrected if needed. The external mass flow sensor is attached to the inlet 2 or outlet 3 of the pump assembly 1 to be able to measure the same flow as the first mass flow sensor 6. The external mass flow sensor (not shown) is preferably connected via a USB port (17) in the pump assembly 1 and is controlled by the CPU 9.

Figure 7:
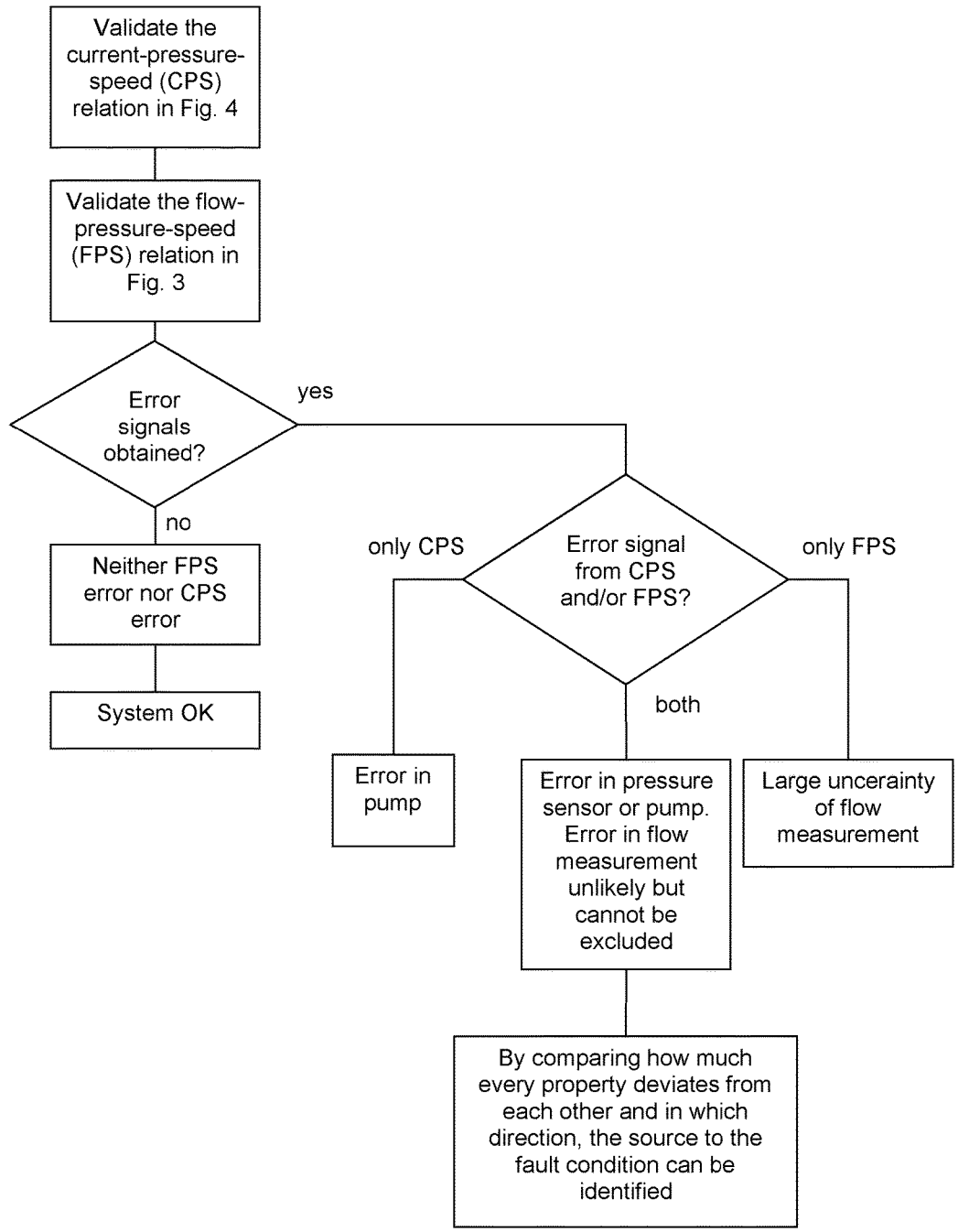
FIG. 7 is a flow chart showing how the sensors in the pump assembly can be used to discover errors in measured values.

FIG. 7 is a flow chart showing how the relationships of the methods described under FIGS. 3 and 4 can be used in combination to discover measurement errors and further also estimate what sensor is causing the error. The method utilizing the relationship between the three properties, i.e. pump current consumption, differential pressure as measured by the first and second pressure sensors, and the pump operational speed (the CPS-relationship) is utilized together with the method using the relationship between the three properties, i.e. the mass flow, differential pressure as measured by the first and second pressure sensors, and the pump operational Speed, (the FPS-relationship). If neither of the methods using the CPS and FPS relationships indicates sensor error, the system is considered to be in good shape. If only the method using the CPS relationship indicates an error, the error is likely to be in the pump. If only the method using the FPS relationship indicates an error, the error is likely to be in the mass flow sensor. If both the methods using the CPS and the FPS relationships indicate error, it is likely that the pressure sensor or the pump sensor is malfunctioning. However, an error in the mass flow sensor cannot be excluded. By comparing how much every measured property deviates from calculated values using other sensors and in which direction the values deviate, the source to the fault condition may in most cases be identified.

Figure 8:
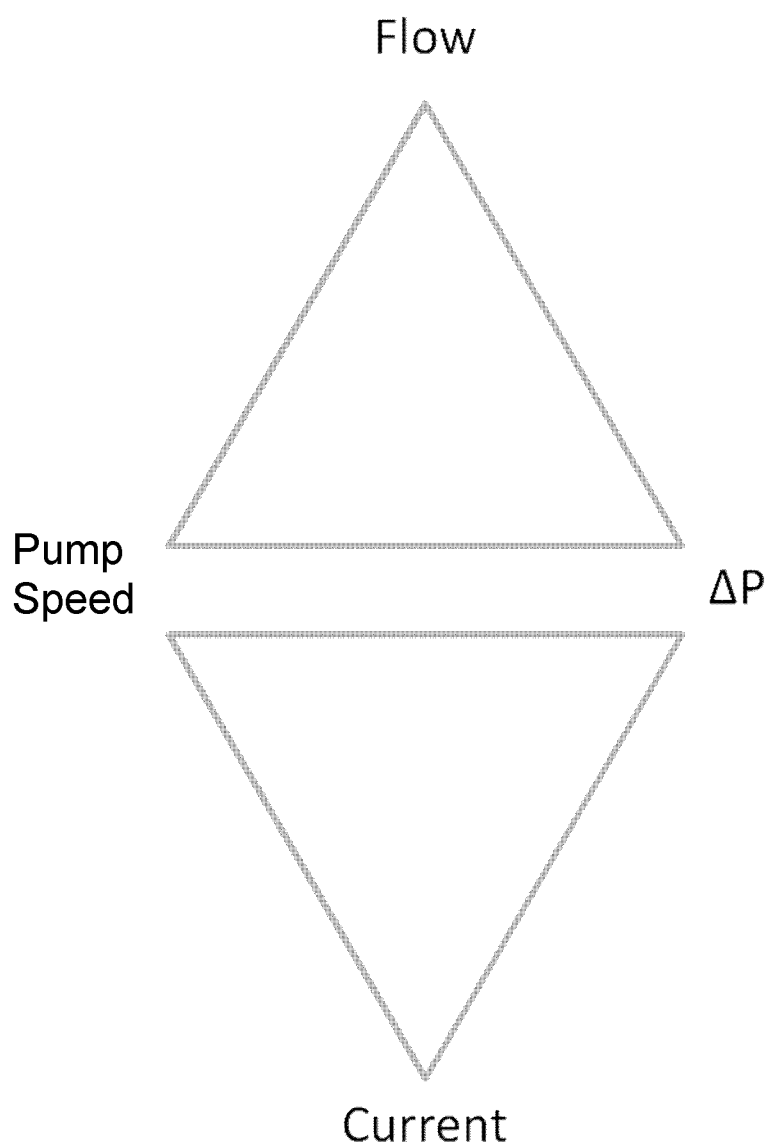
FIG. 8 is a principal sketch of the correlation between the relationships described in FIG. 3 and FIG. 4.

FIG. 8 is a principal sketch showing how the FPS and the CPS interrelate with each other. If the an error is detected in one the FPS triangle sensors, the CPS triangle can be used to find out which one of the sensors that has an error. Analogously, if an error is detected in one of the CPS triangle sensors, the CPS triangle can be used to find out which one of the sensors that has an error in accordance with the method described under FIG. 7.

It is understood that other variations in the present invention are contemplated and in some instances, some features of the invention can be employed without a corresponding use of other features. Accordingly, it is appropriate that the appended claims be construed broadly in a manner consistent with the scope of the invention.

The invention claimed is:

1. A method for verification of correct function of sampling equipment, wherein said method comprises the steps of:
   a) providing a pump assembly comprising
      an inlet and an outlet,
      a flow channel extending between said inlet and outlet,
      a first mass flow sensor located inside said flow channel,
      a first pressure sensor located near said first mass flow sensor adapted to measure a first pressure inside said flow channel,
      a pump located along said flow channel downstream of the first the first pressure sensor, wherein the pump is adapted to force a gas flow through said flow channel, and
      a second pressure sensor located outside said flow channel, said second pressure sensor being adapted to measure a second pressure being the ambient atmospheric pressure,
   b) calculating the pressure difference between said first pressure and said second pressure,
   c) calculating any error in an output signal from the first mass flow meter by comparing said pressure difference with a value in a pre-calibrated table of mass flow output signal values as a function of said pressure difference, and d) providing an error signal comprising a value of said calculated error if said value of said calculated error is above a predetermined threshold; and wherein the method further comprising the steps of
providing an error signal if the calculated pressure difference exceeds a pre-determined value, thereby indicating a clogged or blocked sampling device, and
providing an error signal if the calculated pressure difference is below a pre-determined value, thereby indicating a broken and/or leaking sampling device.

2. The method according to claim 1, further comprising the step of adjusting the output signal from the first mass flow sensor if the calculated error is below said predetermined threshold.

3. The method according to claim 1, wherein the pump assembly is connected to a sampling device, through which the gas flow is drawn by use of the pump assembly.

4. The method according to claim 3, further comprising the steps of measuring the backpressure induced by the sampling device, calculating its restriction and evaluating the condition of the sampling device, and logging said restriction and said evaluated condition to a memory.

5. The method according to claim 1, wherein said pump assembly further comprises an inlet filter, and an outlet filter, and wherein the method further comprises the step of providing an error signal if the calculated pressure difference is below a pre-determined value, thereby indicating a broken inlet or outlet filter of the pump assembly.

6. The method according to claim 1, wherein the pump assembly further comprises an ambient temperature sensor, wherein the method further comprises the steps of:
measuring the ambient temperature with the ambient temperature sensor,
measuring the temperature in the flow channel using a reference temperature measurement provided by the mass flow sensor,
calculating the temperature difference between the measured ambient temperature and the measured reference temperature in the flow channel, and
providing an error signal if the calculated temperature difference is above a predetermined threshold.

7. The method according to claim 6, further comprising the step of manually setting the ambient temperature value to be used in calculations to a certain value.

8. The method according to claim 1, wherein the pump assembly further comprises an ambient temperature sensor, wherein the method further comprises the step of calculating the volumetric flow from the measured mass flow and the measured ambient temperature by use of the ideal gas law.

9. The method according to claim 1, wherein it further comprises the steps of:
detachably connecting a second mass flow sensor to said outlet or inlet,
measuring a first mass flow with the first mass flow sensor and a second mass flow with the second mass flow sensor,
calculating the difference between the values of said first and second mass flows, and
providing an output signal representing said calculated difference.

10. The method according to claim 9, further comprising the step of adjusting the output signal of the first mass flow meter to compensate for said calculated difference.

11. The method according to claim 1, wherein said pump assembly further comprises a memory and wherein the method further comprises logging at least one of the values of the ambient temperature, first mass flow, second mass flow, first pressure, second pressure, reference temperature and any calculated error by writing the respective time and value to said memory.

12. The method according to claim 1, wherein one or more pump assemblies are communicatively connected to a controlling device.

13. The method according to claim 1, wherein one or more pump assemblies are communicatively connected to each other.

14. The method according to claim 1, wherein said pump assembly further comprises:
a central processing unit (CPU), and
a memory,
wherein all method steps are instructions in a computer program stored in said memory, said computer program being executed by said CPU, and
wherein all calculations steps are performed by execution of said computer program by said CPU.

15. A method for verification of correct function of sampling equipment, wherein said method comprises the steps of:
a) providing a pump assembly comprising
an inlet and an outlet,
a flow channel extending between said inlet and outlet,
a pump located along said flow channel adapted to force a gas flow through said flow channel,
a pump operational speed sensor,
a first mass flow sensor located inside said flow channel,
a first pressure sensor located near said first mass flow sensor adapted to measure a first pressure inside said flow channel,
a second pressure sensor located outside said flow channel, said second pressure sensor being adapted to measure a second pressure being the ambient atmospheric pressure;
b) measuring a first property from among a group of three properties consisting of:
a mass flow using the first mass flow sensor,
a differential pressure using said first pressure sensor and said second pressure sensor, and
a pump operational speed using said pump operational speed sensor;
c) measuring a second property from among said group of three properties, the second property being different from the first property;
d) calculating an approximated value of the third property not measured in b) and c) from the properties measured in b) and c);
e) measuring the third property not measured in b) and c);
f) calculating a difference between the approximated value of the third property and the measured value of the third property; and
g) providing an error signal indicating that said sampling equipment does not function correctly if said calculated difference exceeds a predetermined value.

16. A method for verification of correct function of sampling equipment, wherein said method comprises the steps of:
a) providing a pump assembly comprising
an inlet and an outlet,
a flow channel extending between said inlet and outlet, a pump located along said flow channel adapted to force a gas flow through said flow channel,
a pump operational speed sensor,
a pump current consumption sensor measuring a current consumption of said pump,
a first mass flow sensor located inside said flow channel,
a first pressure sensor located near said first mass flow sensor adapted to measure a first pressure inside said flow channel,
a second pressure sensor located outside said flow channel, said second pressure sensor being adapted to measure a second pressure being the ambient atmospheric pressure;

b) measuring a first property from among a group of three properties consisting of:
a pump current consumption using said pump current consumption sensor,
a differential pressure using said first pressure sensor and said second pressure sensor, and
a pump operational speed using said pump operational speed sensor;

c) measuring a second property from among said group of three properties, the second property being different from the first property;

d) calculating an approximated value of the third property not measured in b) and c) from the properties measured in b) and c);

e) measuring the third property not measured in b) and c);

f) calculating a difference between the approximated value of the third property and the measured value of the third property; and g) providing an error signal indicating that said sampling equipment does not function correctly if said calculated difference exceeds a predetermined value.

17. A method for verification of correct function of sampling equipment, wherein said method comprises the steps of:

a) providing a pump assembly comprising
an inlet and an outlet,
a flow channel extending between said inlet and outlet,
a pump located along said flow channel adapted to force a gas flow through said flow channel,
a pump operational speed sensor,
a pump current consumption sensor measuring a current consumption of said pump,
a first mass flow sensor located inside said flow channel,
a first pressure sensor located near said first mass flow sensor adapted to measure a first pressure inside said flow channel,
a second pressure sensor located outside said flow channel, said second pressure sensor being adapted to measure a second pressure being the ambient atmospheric pressure;

b) measuring a first property from among a first group of three properties consisting of:
a mass flow using the first mass flow sensor,
a differential pressure using said first pressure sensor and said second pressure sensor, and
a pump operational speed using said pump operational speed sensor;

c) measuring a second property from among said first group of three properties, the second property being different from the first property;

d) calculating an approximated value of the third property from among said first group of three properties not measured in b) and c) from the properties measured in b) and c);

e) measuring the third property not measured in b) and c);

f) calculating a first difference between the value of the third property approximated in d) and the value of the third property measured in e);

g) providing a first error signal indicating that said sampling equipment does not function correctly if said calculated first difference exceeds a predetermined value;

h) measuring a first property from among a second group of three properties consisting of:
a pump current consumption using said pump current consumption sensor,
a differential pressure using said first pressure sensor and said second pressure sensor, and
a pump operational speed using said pump operational speed sensor;

i) measuring a second property from among said second group of three properties, the second property being different from the first property;

j) calculating an approximated value of the third property from among said second group of three properties not measured in h) and i) from the properties measured in h) and i);

k) measuring the third property not measured in h) and i);

l) calculating a second difference between the value of the third property approximated in j) and the value of the third property measured in k);

m) providing a second error signal indicating that said sampling equipment does not function correctly if said calculated second difference exceeds a predetermined value n) if both the first error signal and the second error signal are provided, providing a third error signal indicating that the pressure sensor or the pump is damaged;

o) if the first error signal is provided but the second error signal is not provided, providing a fourth error signal indicating uncertain flow measurements; and p) if the first error signal is not provided while the second error signal is provided, providing a fifth error signal indicating an error in the pump.

* * * * *